United States Patent
Proksch et al.

(10) Patent No.: US 12,285,153 B2
(45) Date of Patent: Apr. 29, 2025

(54) ANATOMICAL SCENE VISUALIZATION SYSTEMS AND METHODS

(71) Applicant: Intuitive Surgical Operations, Inc., Sunnyvale, CA (US)

(72) Inventors: Daniel Proksch, San Jose, CA (US); Mahdi Azizian, San Jose, CA (US); Pourya Shirazian, Menlo Park, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 181 days.

(21) Appl. No.: 17/928,493

(22) PCT Filed: May 27, 2021

(86) PCT No.: PCT/US2021/034411
§ 371 (c)(1),
(2) Date: Nov. 29, 2022

(87) PCT Pub. No.: WO2021/247349
PCT Pub. Date: Dec. 9, 2021

(65) Prior Publication Data
US 2023/0277035 A1    Sep. 7, 2023

Related U.S. Application Data

(60) Provisional application No. 63/033,668, filed on Jun. 2, 2020.

(51) Int. Cl.
*A61B 1/00* (2006.01)
*G06T 7/70* (2017.01)
*G06T 11/00* (2006.01)

(52) U.S. Cl.
CPC .............. *A61B 1/0005* (2013.01); *G06T 7/70* (2017.01); *G06T 11/00* (2013.01);
(Continued)

(58) Field of Classification Search
None
See application file for complete search history.

(56) References Cited

U.S. PATENT DOCUMENTS

2014/0303491 A1   10/2014   Shekhar et al.
2019/0060001 A1*   2/2019   Kohli ..................... A61B 34/20
(Continued)

FOREIGN PATENT DOCUMENTS

WO   WO-2019152269 A1   8/2019

OTHER PUBLICATIONS

International Preliminary Report on Patentability for Application No. PCT/US2021/034411 mailed Dec. 15, 2022, 09 pages.
(Continued)

*Primary Examiner* — Sultana M Zalalee

(57) ABSTRACT

An illustrative system may be configured to obtain a visual image of an anatomical scene that includes an imaging probe and to augment the visual image with a synthetic element that indicates, within the visual image, an area of the anatomical scene being imaged by the imaging probe. The synthetic element may include spatial markers. The visualization system may be further configured to direct a display device to display the augmented image. The visualization system may be further configured to direct the display device to display, at a position outside of the synthetic element, a probe image captured by the imaging probe.

20 Claims, 14 Drawing Sheets

(52) U.S. Cl.
CPC ............... *G06T 2207/10068* (2013.01); *G06T 2207/30004* (2013.01); *G06T 2210/41* (2013.01)

(56) References Cited

U.S. PATENT DOCUMENTS

| | | | |
|---|---|---|---|
| 2019/0223958 A1* | 7/2019 | Kohli | A61B 8/4427 |
| 2019/0247130 A1* | 8/2019 | State | A61B 34/20 |
| 2019/0290247 A1* | 9/2019 | Popovic | A61B 1/0005 |
| 2019/0365350 A1* | 12/2019 | Chiang | A61B 8/469 |
| 2020/0015910 A1* | 1/2020 | Azizian | A61B 34/20 |
| 2020/0388075 A1 | 12/2020 | Kazanzides et al. | |
| 2021/0137492 A1* | 5/2021 | Imai | A61B 8/4254 |
| 2021/0236091 A1* | 8/2021 | Tsuruta | A61B 8/469 |

OTHER PUBLICATIONS

International Search Report and Written Opinion for Application No. PCT/US2021/034411, mailed on Aug. 27, 2021, 12 pages.
Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.

* cited by examiner

ANATOMICAL SCENE VISUALIZATION SYSTEMS AND METHODS

RELATED APPLICATIONS

The present application is a U.S. National Stage Application under 35 U.S.C. 8371 of International Application No. PCT/US2021/034411, filed on May 27, 2021, which claims priority to U.S. Provisional Patent Application No. 63/033,668, filed Jun. 2, 2020, the contents of which are hereby incorporated by reference in their entirety.

BACKGROUND INFORMATION

During a medical procedure, an imaging modality such as an endoscope may be used to capture imagery of an anatomical scene. In some scenarios, one or more additional imaging modalities may be used to capture additional imagery of the anatomical scene that may also be presented to the medical team member. For example, an ultrasound scan, an optical coherence tomography (OCT) scan, and a rapid evaporative ionization mass spectrometry (REIMS) scan are other imaging modalities that may be used to capture imagery of the anatomical scene. Imagery captured by different imaging modalities may be presented to a medical team member (e.g., a nurse, a surgeon, etc.) such that the medical team member may view visualizations of the anatomical scene while performing the medical procedure.

SUMMARY

The following description presents a simplified summary of one or more aspects of the systems and methods described herein. This summary is not an extensive overview of all contemplated aspects and is intended to neither identify key or critical elements of all aspects nor delineate the scope of any or all aspects. Its sole purpose is to present one or more aspects of the systems and methods described herein as a prelude to the detailed description that is presented below.

An illustrative system includes a memory storing instructions and a processor communicatively coupled to the memory and configured to execute the instructions to: obtain a visual image of an anatomical scene that includes an imaging probe; augment the visual image with a synthetic element that indicates, within the visual image, an area of the anatomical scene being imaged by the imaging probe, the synthetic element including spatial markers within the area; and direct a display device to display the augmented image.

Another illustrative system includes a memory storing instructions and a processor communicatively coupled to the memory and configured to execute the instructions to: obtain a visual image of an anatomical scene that includes an imaging probe; obtain a probe image captured by the imaging probe; augment the visual image with a synthetic element that indicates, within the visual image, an area of the anatomical scene being imaged by the imaging probe; and direct a display device to display the augmented image and the probe image, the probe image positioned outside of the synthetic element.

An illustrative method includes: obtaining a visual image of an anatomical scene that includes an imaging probe; augmenting the visual image with a synthetic element that indicates, within the visual image, an area of the anatomical scene being imaged by the imaging probe, the synthetic element including spatial markers within the area; and directing a display device to display the augmented image.

Another illustrative method includes: obtaining a visual image of an anatomical scene that includes an imaging probe; obtaining a probe image captured by the imaging probe; augmenting the visual image with a synthetic element that indicates, within the visual image, an area of the anatomical scene being imaged by the imaging probe; and directing a display device to display the augmented image and the probe image, the probe image positioned outside of the synthetic element.

An illustrative non-transitory computer-readable medium stores instructions that, when executed, direct a processor of a computing device to: obtain a visual image of an anatomical scene that includes an imaging probe; augment the visual image with a synthetic element that indicates, within the visual image, an area of the anatomical scene being imaged by the imaging probe, the synthetic element including spatial markers within the area; and direct a display device to display the augmented image.

Another illustrative non-transitory computer-readable medium stores instructions that, when executed, direct a processor of a computing device to: obtain a visual image of an anatomical scene that includes an imaging probe; obtain a probe image captured by the imaging probe; augment the visual image with a synthetic element that indicates, within the visual image, an area of the anatomical scene being imaged by the imaging probe; and direct a display device to display the augmented image and the probe image, the probe image positioned outside of the synthetic element.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Figure 1:
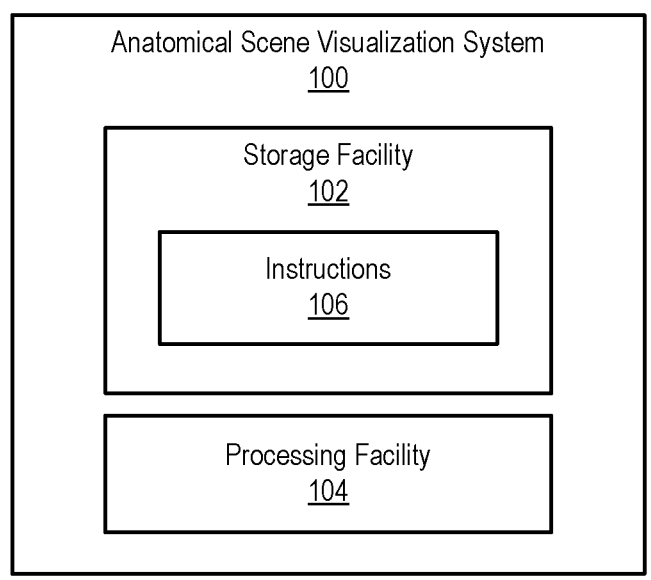
FIG. 1 depicts an illustrative anatomical scene visualization system according to principles described herein.

Anatomical scene visualization systems and methods are described herein. The systems and methods are configured to augment one or more visual images of an anatomical scene and provide display images including the augmented images for display in any of the ways described herein. In certain examples, an anatomical scene visualization system ("visualization system") may be configured to augment a visual image of an anatomical scene, which visual image is captured by a first imaging modality such as an endoscope, with a synthetic element that indicates an area of the anatomical scene being imaged by a second imaging modality such as an imaging probe at the anatomical scene (e.g., an ultrasound probe positioned at the anatomical scene). The synthetic element may assist a user (e.g., a medical team member) who is viewing the augmented image in identifying the area of the anatomical scene being imaged by the imaging probe while allowing at least part of the area, as depicted in the visual image captured by the first imaging modality, to remain visible in the augmented visual image (e.g., by not substantially occluding the area being imaged by the imaging probe as depicted in the visual image captured by the first imaging modality).

As used herein, a synthetic element refers to a graphical element that may be added to an image captured by an imaging device. The synthetic element may be added to the image to form an augmented image that includes the image augmented with the synthetic element. The synthetic element may be added to the image in any suitable way, such as by overlaying the synthetic element on the image, integrating the synthetic element into the image, etc. Illustrative examples of images of an anatomical scene augmented with synthetic elements and content associated with synthetic elements are described herein.

In certain examples, the visualization system may be configured to provide, for display by a display device, an augmented image (e.g., a visual image augmented with a synthetic element) together with a probe image captured by the imaging probe. The probe image may be positioned outside of the synthetic element such that the probe image does not overlap the synthetic element or a depiction, in the visual image, of the area of the anatomical scene being imaged by the imaging probe. As an example, the probe image may be presented in a corner area of the visual image to avoid interfering with (e.g., occluding) a view of the area of the anatomical scene being imaged by the imaging probe, as represented in the visual image. As another example, the probe image may be presented outside of the visual image (e.g., together with the visual image but not overlapping the visual image in a display view). The probe image may assist the user who is viewing a display image in concurrently viewing both the probe image and the area of the anatomical scene being imaged by the imaging probe as depicted in the visual image captured by the first imaging modality. Illustrative examples of such display images are described herein.

In certain examples, the visualization system may be configured to augment the visual image with a preview placeholder indicating a display position for a probe image to be captured by the imaging probe. The preview placeholder may represent a location (e.g., a location on the visual image of the anatomical scene) where a probe image to be captured by the imaging probe may be presented. The preview placeholder may assist the user who is viewing the augmented image in making any desired adjustments before a probe image is captured and presented, such as by adjusting a viewpoint of a first imaging modality such as an endoscope capturing images of the anatomical scene.

Systems and methods described herein may provide various advantages and benefits. For example, systems and methods described herein may provide visualization of an anatomical scene that may be visually realistic and/or intuitive to a medical team member (e.g., a surgeon), may reduce the complexity of the medical procedure for the medical team member, and/or may allow the medical team member to concurrently, conveniently, and/or intuitively visualize imagery captured by different imaging modalities (e.g., imagery of surface and subsurface anatomy). In certain examples, one or more visualizations may facilitate accurate, efficient, and/or intuitive operation of an imaging probe at an anatomical scene. These and other advantages and benefits of systems and methods described herein will be made apparent.

FIG. 1 depicts an illustrative anatomical scene visualization system 100 ("system 100") configured to perform operations to provide anatomical scene visualizations including any of the illustrative examples of anatomical scene visualizations described herein. In certain examples, system 100 may be configured to augment a visual image of an anatomical scene, which visual image is captured by a first imaging modality such as an endoscope, in any of the ways described herein. System 100 may be included in, implemented by, or connected to one or more components of a computer-assisted medical system. For example, system 100 may be implemented by one or more components of a computer-assisted medical system. As another example, system 100 may be implemented by a stand-alone computing system communicatively coupled to a computer-assisted medical system. An illustrative computer-assisted medical system is described further below.

System 100 may include a storage facility 102 and a processing facility 104 selectively and communicatively coupled to one another. Each of facilities 102 and 104 may include or be implemented by one or more physical computing devices including hardware and/or software components such as processors, memories, storage drives, communication interfaces, instructions stored in memory for execution by the processors, and so forth. Although facilities 102 and 104 are shown to be separate facilities in FIG. 1, facilities 102 and 104 may be combined into a single facility or divided into more facilities as may serve a particular implementation. In some examples, each of facilities 102 and 104 may be distributed between multiple devices and/or multiple locations as may serve a particular implementation.

Storage facility 102 may maintain (e.g., store) executable data used by processing facility 104 to perform one or more of the operations described herein. For example, storage facility 102 may store instructions 106 that may be executed by processing facility 104 to perform one or more of the operations described herein. Instructions 106 may be implemented by any suitable application, software, code, and/or other executable data instance. Storage facility 102 may also maintain any data received, generated, managed, used, and/or transmitted by processing facility 104.

Processing facility 104 may be configured to perform (e.g., execute instructions 106 stored in storage facility 102 to perform) various operations associated with providing anatomical scene visualizations including any of illustrative visualizations described herein. Examples of such operations will now be described in additional detail with reference to the remaining figures. In the description that follows, any references to operations performed by system 100 may be understood to be performed by processing facility 104 of system 100.

Figure 2:
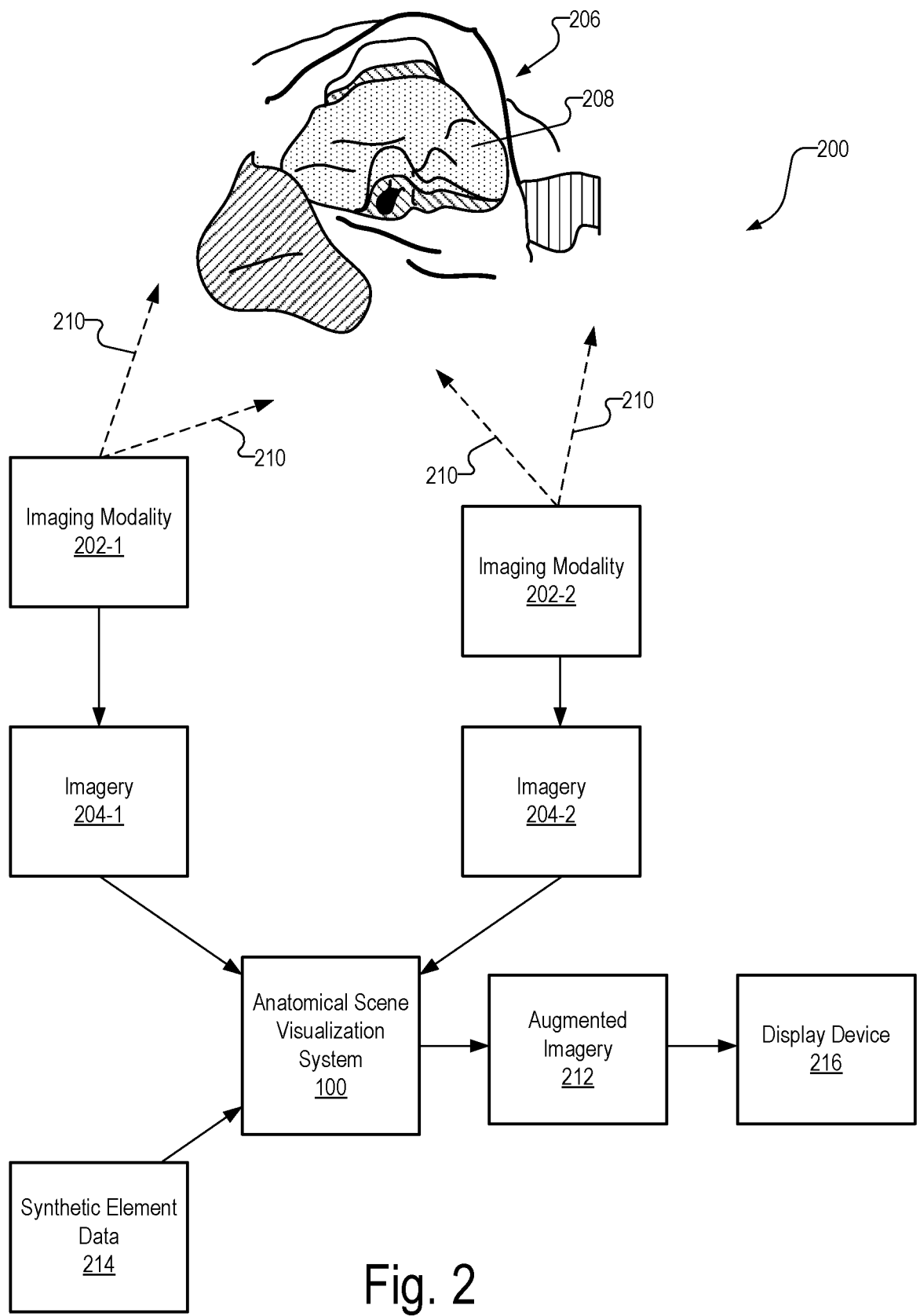
FIG. 2 depicts the anatomical scene visualization system of FIG. 1 configured to generate augmented imagery of an anatomical scene according to principles described herein.

FIG. 2 depicts a configuration 200 in which system 100 is configured to generate augmented imagery of an anatomical scene. As shown, configuration 200 may include multiple imaging modalities 202 (e.g., imaging modalities 202-1 and 202-2) configured to capture imagery 204 (e.g., imagery 204-1 captured by imaging modality 202-1 and imagery 204-2 captured by imaging modality 202-2) of an anatomical scene 206.

Anatomical scene 206 may include any volumetric space associated with anatomy, such as a volumetric space associated with a medical procedure. For example, anatomical scene 206 may include any part or parts of a body, such as anatomy 208 (e.g., tissue, etc.) of the body of a patient in a space associated with the medical procedure. Anatomical scene 206 may, in certain examples, be entirely disposed within a body and may include a space within the body near where a medical procedure is planned to be performed, is being performed, or has been performed. For example, for a minimally invasive medical procedure being performed on tissue internal to a patient, anatomical scene 206 may include the tissue, anatomy underlying the tissue, as well as space around the tissue where, for example, medical instruments being used to perform the medical procedure are located. In other examples, anatomical scene 206 may be at least partially disposed external to a body. For instance, for an open medical procedure being performed on a patient, part of anatomical scene 206 (e.g., tissue being operated on) may be internal to the patient while another part of anatomical scene 206 (e.g., a space around the tissue where one or more medical instruments may be disposed) may be external to the patient. Anatomical scene 206 may include a workspace in which a medical procedure is performed, such as an actual, real-world workspace associated with a patient and in which one or more medical instruments are used to perform the medical procedure on the patient. In certain examples, an anatomical scene associated with a medical procedure such as a surgical procedure may be referred to as a "medical scene" or a "surgical scene."

As used herein, a medical procedure may include any procedure associated with anatomy, including any diagnostic or treatment procedure (e.g., a surgical procedure, a therapeutic procedure, etc.) in which manual, tele-operated, computer-assisted, and/or instrumental techniques are used on a patient to investigate or treat a physical condition of the patient. A medical procedure may refer to any phases of a medical procedure, such as preoperative, operative (i.e., intraoperative), and postoperative phases of a medical procedure.

Imaging modalities 202 may be configured and/or used to capture imagery 204 of anatomical scene 206. Such a capture is represented by dashed lines 210 in FIG. 2. Imaging modalities 202 may each capture imagery 204 of anatomical scene 206 in any suitable manner and at any suitable time. Accordingly, one or more imaging modalities 202 may capture imagery 204 of anatomical scene 206 during one or more preoperative, intraoperative, and/or postoperative phases of a medical procedure.

Imaging modalities 202 may include any set of different imaging modalities that may be used to capture imagery of an anatomical scene. Examples of imaging modalities 204 include, without limitation, endoscopic imaging by an endoscope, ultrasound imaging by an ultrasound machine, optical coherence tomography (OCT) imaging by an OCT machine, and rapid evaporative ionization mass spectrometry (REIMS) imaging by a REIMS machine. Any suitable additional or alternative imaging modalities may be used in other examples. In certain implementations, imaging modality 202-1 may include endoscopic imaging by an endoscope, and imaging modality 202-2 may include any different imaging modality such as ultrasound imaging by an ultrasound machine (e.g., an ultrasound probe), OCT imaging by an OCT machine, or REIMS imaging by a REIMS machine. In such implementations, imaging modality 202-1 may capture imagery 204-1 that is endoscopic imagery of anatomical scene 206, and imaging modality 202-2 may capture imagery 204-2 that is ultrasound imagery, OCT imagery, or REIMS imagery of anatomical scene 206. In certain implementations, imaging modality 202-2 is an imaging probe located in anatomical scene 206, such as an ultrasound probe in anatomical scene 206.

In certain examples, imaging modality 202-1 may be configured to capture imagery of surface anatomy included in anatomical scene 206 (e.g., an outer surface of tissue included in the anatomical scene), and imaging modality 202-2 may be configured to capture imagery of subsurface anatomy included in anatomical scene 206 (e.g., subsurface tissue that is behind the outer surface of tissue included in the anatomical scene). For example, imaging modality 202-1 may include endoscopic imaging by an endoscope that captures images of surface tissue within a patient, and imaging modality 202-2 may include ultrasound, OCT, or REIMS imaging that captures images of subsurface tissue that, from the perspective of the endoscope, is behind and hidden from the view of the endoscope by the surface tissue within the patient.

Imagery 204 of anatomical scene 206 may include images of anatomical scene 206 captured by imaging modalities 202. For example, imagery 204 may include endoscopic images, ultrasound images, OCT images, REIMS images, and/or any other suitable form of images of anatomical scene 206. Imagery 204 may include any suitable type of images represented by data in any suitable data format. For example, imagery 204 may include still-frame images, video, color images, infrared images, depth images, hyperspectral images, and/or any other type of images that may visually represent anatomical scene 206. An image captured by an imaging modality may include a grid of pixels having values (e.g., color values, brightness values, etc.) representative of an appearance of anatomical scene 206 as captured by the imaging modality. Color values for pixels in a captured image may represent actual, organic colors of the anatomical scene as captured by an imaging modality.

Additionally or alternatively, imagery 204 may include one or more models of anatomical scene 206 that are generated based on imaging performed by an imaging modality. For example, imagery 204 may include a three-dimensional (3D) model of anatomical scene 206 that is generated based on imaging performed by an imaging modality, such as imaging performed by an ultrasound machine, an OCT machine, a REIMS machine, or other suitable imaging modality. The 3D model may be a full volumetric model that includes voxels (i.e., volumetric pixels) having values (e.g., color values, brightness values, etc.) representative of an appearance of anatomical scene 206 at 3D points within the model. Such a volumetric model may facilitate any slice of the 3D model being identified and used by system 100 to produce an image of the slice of the 3D model. Color values for pixels in the slice image may represent actual, organic colors of the anatomical scene as captured by an imaging modality.

While FIG. 2 depicts two imaging modalities 202-1 and 202-2 respectively capturing imagery 204-1 and 204-2 that are provided as input to system 100, other examples may include any suitable number and/or configuration of multiple, different imaging modalities that capture imagery that is provided as input to system 100 for use in generating augmented imagery of anatomical scene 206. For example, three or more different imaging modalities may capture imagery that is input to system 100 for use in generating augmented imagery of anatomical scene 206.

System 100 may generate augmented imagery 212 of anatomical scene 206 based on imagery 204 captured by one or more imaging modalities 202. System 100 may do this in any of the ways described herein to generate an augmented image that includes a visual image of anatomical scene 206 as captured by an imaging modality (e.g., imaging modality 202-1) augmented with one or more synthetic elements and/or with imagery captured by another imaging modality (e.g., imaging modality 202-2). For example, system 100 may obtain a visual image of anatomical scene captured by imaging modality 202-1 and augment the visual image in any of the ways described herein to form an augmented image. To this end, system 100 may access and use synthetic element data 214 representing one or more synthetic elements to augment the visual image with one or more synthetic elements. Additionally or alternatively, system 100 may access and use imagery 204-2 captured by imaging modality 202-2 to augment the visual image with the imagery 204-2. Examples of augmented images and how the augmented images may be generated by system 100 are described herein.

System 100 may direct a display device 216 to display augmented imagery 212. For example, system 100 may provide data representative of augmented imagery 212 to display device 216, which may be configured to display augmented imagery 212 for viewing by a user of a computer-assisted medical system. Display device 216 may include any device capable of receiving and processing imagery data to display one or more images. To this end, display device 216 may include one or more display screens on which images may be displayed. In certain examples, display device 216 may be a component of or communicatively connected to a computer-assisted medical system.

Figure 3A:
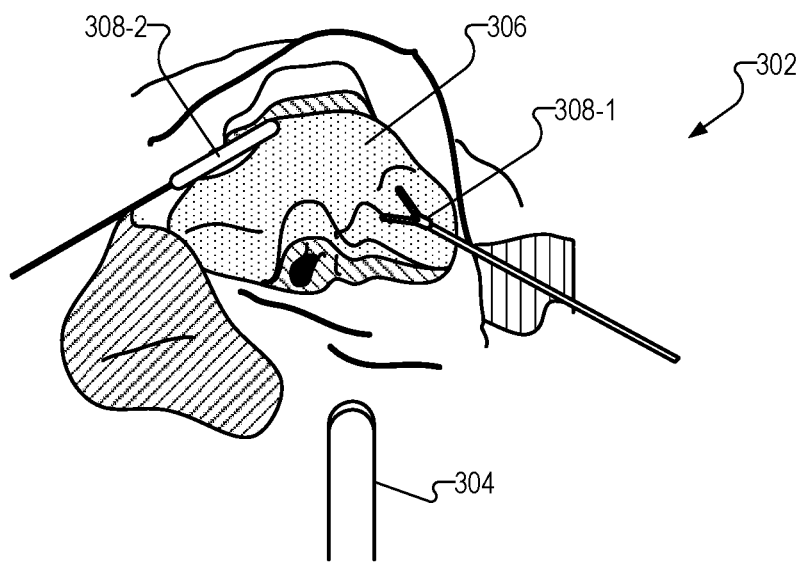
FIG. 3A depicts an illustrative anatomical scene according to principles described herein.

Illustrative examples of augmented images of an anatomical scene and ways of generating the augmented images will now be described with reference to FIGS. 3A-7B. FIG. 3A depicts an anatomical scene 302 being imaged by an endoscope 304. Anatomical scene 302 may be a real-world physical workspace located in front of endoscope 304 configured to capture endoscopic imagery of the scene. In certain examples, anatomical scene 302 may include anatomy 306 of a patient and one or more medical instruments positioned relative to anatomy 306 in anatomical scene 302. In the illustrated example, a grasper tool 308-1 and an imaging probe 308-2 are in anatomical scene 302.

Figure 3B:
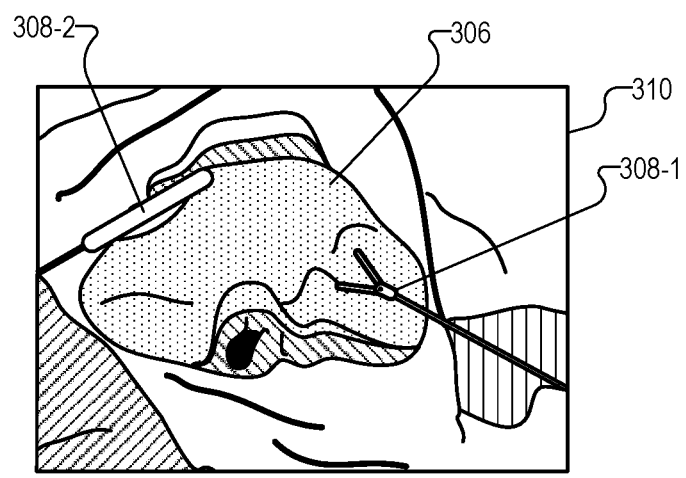
FIG. 3B depicts an illustrative visual image of the anatomical scene of FIG. 3A according to principles described herein.

System 100 may obtain an image of anatomical scene 302. For example, system 100 may access a visual image of anatomical scene 302 as captured by endoscope 304 and provide the visual image for display by a display device. FIG. 3B depicts an example of a visual image 310 of the anatomical scene 302 as captured by endoscope 304 and displayed by a display device. System 100 may augment visual image 310, in any of the ways described herein, to generate an augmented image of anatomical scene 302. Illustrative augmentations of visual image 310 will now be described. While the examples are described with reference to visual image 310, the augmentations may be applied to any other image of an anatomical scene.

Figure 4A:
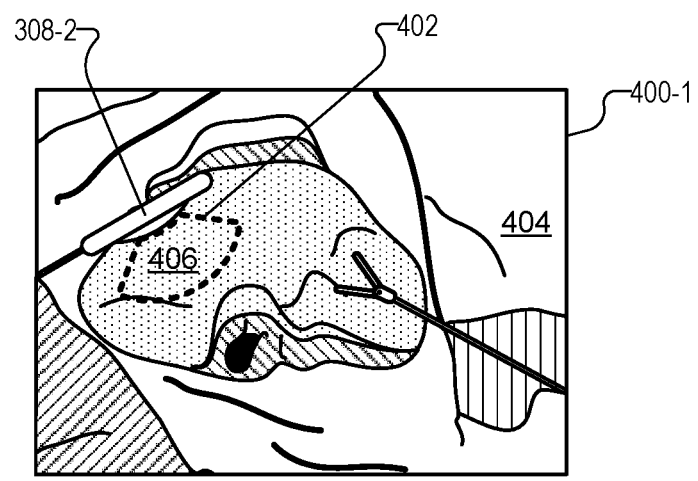
FIGS. 4A-7B depict illustrative augmented images of the anatomical scene of FIG. 3A according to principles described herein.

FIG. 4A depicts an illustrative augmented image 400-1 that may be generated by system 100 and displayed by a display device. Augmented image 400-1 may be a visual image of an anatomical scene captured by a first imaging modality and augmented with a synthetic element 402 that is positioned relative to a depiction of the anatomical scene in the visual image. For example, as shown, augmented image 400-1 may be visual image 310 of anatomical scene 302 captured by endoscope 304 and augmented with synthetic element 402. Synthetic element 402 indicates, within the visual image, an area of the anatomical scene being imaged by an imaging probe such as imaging probe 308-2. The imaging probe may capture imagery using a second imaging modality, and the area of the anatomical scene being imaged by the imaging probe may be referred to as the "probe imaging area."

Synthetic element 402 may augment the visual image of the anatomical scene captured by the first imaging modality without undesirably interfering with a view of the probe imaging area as depicted in the visual image of the anatomical scene captured by the first imaging modality (e.g., without substantially occluding from view the probe imaging area as depicted in the visual image of the anatomical scene captured by the first imaging modality). To that end, synthetic element 402 may be configured to allow at least part of the area of the anatomical scene being imaged by the imaging probe, as represented by the visual image, to remain visible in the augmented visual image. Accordingly, a medical team member viewing augmented image 400-1 may view, within the visual image of the anatomical scene, a representation of the probe imaging area within the anatomical scene as synthetic element 402 indicates the probe imaging area without substantial interference to (e.g., occlusion of) the presentation of the probe imaging area as imaged by the first imaging modality.

Synthetic element 402 may be any suitable shape and may include any suitable graphical element or elements that define, within augmented image 400-1, an area being imaged by the imaging probe at the anatomical scene. For example, synthetic element 402 may be a circle, an oval, a quadrilateral (e.g., a rectangle, a fan), a triangle, or any other suitable shape. Synthetic element 402 may include any graphical element or elements that provide a suitable visual representation of the probe imaging area. Synthetic element 402 may indicate a boundary of the area being imaged by the imaging probe at the anatomical scene. For example, synthetic element 402 may include a border element outlining, within the visual image, the area of the anatomical scene being imaged by the imaging probe. The border element may be any suitable shape and may be represented by any suitable visual representation such as solid lines, dashed lines, arcs, and/or the like arranged to indicate a boundary of the probe imaging area.

As shown in FIG. 4A, the position of synthetic element 402 within augmented image 400-1 may define two regions of augmented image 400-1-a first region 404 that is outside synthetic element 402 and a second region 406 that is inside synthetic element 402. Both first and second regions 404 and 406 of augmented image 400-1 may include representations of the anatomical scene as captured by a first imaging modality (e.g., endoscope 304). The area within the second region 406 may include a depiction of the probe imaging area as captured by the first imaging modality. In certain examples, the area within the second region 406 may exclusively include only a depiction of the probe imaging area as captured by the first imaging modality. In other examples, additional content (e.g., content associated with synthetic element 402, the probe imaging area, and/or a probe image captured by the imaging probe) may be provided within first region 404 and/or second region 406, as will be described herein.

To generate augmented image 400-1, system 100 may determine the probe imaging area of the imaging probe in any suitable way and place synthetic element 402 to indicate, within the visual image captured by the first imaging modality, the probe imaging area. For example, system 100 may determine the probe imaging area based on a pose of the imaging probe (e.g., a position and orientation of the imaging probe using any suitable degrees of freedom) relative to the anatomical scene, parameters of the imaging probe, information associated with the anatomical scene such as depth data, information associated with the first imaging modality (e.g., a viewpoint of endoscope 304), and/or other suitable information about the first imaging modality, the imaging probe, and/or the anatomical scene. System 100 may map the determined probe imaging area to the visual image of the anatomical scene in any suitable way, such as by projecting the probe imaging area from the viewpoint of the first imaging modality to identify second region 406 within the visual image. System 100 may place synthetic element 402 within the visual image to visually indicate the second region 406 and thereby visually indicate, within the visual image, the area being imaged by the imaging probe.

In other examples, system 100 may augment the visual image with synthetic element 402 by placing synthetic element 402 relative to other elements in the anatomical scene. For example, system 100 may determine the position of synthetic element 402 relative to the imaging probe by projecting synthetic element 402 from the imaging probe in a particular manner (e.g., based on the pose of the imaging probe) such that synthetic element 402 is positioned relative to the imaging probe and then projected, from the viewpoint of endoscope 304, to form augmented image 400-1.

In certain implementations, system 100 may access tracking information (e.g., position information, orientation information, movement information, kinematics information, etc.) for the imaging probe from a computer-assisted medical system to which the imaging probe is connected and use the tracking information to determine a pose of the imaging probe at the anatomical scene. Additionally or alternatively, system 100 may access and use vision-based tracking information (e.g., vision-based tracking information derived from imagery captured by the first imaging modality and kinematics information for the first imaging modality) to determine a pose of the imaging probe at the anatomical scene. System 100 may determine the pose of the imaging probe relative to the anatomical scene in any other suitable way in other examples. System 100 may use the tracking information to determine the area being imaged by the imaging probe, such as by using the tracking information to determine a pose of the imaging probe and determining, based on the pose of the imaging probe, the probe imaging area.

In certain examples, system 100 may be configured to select or generate synthetic element 402 to fit the determined probe imaging area and to place the synthetic element 402 relative to the visual image to visually indicate, within the visual image, the probe imaging area as depicted in the visual image. This may include system 100 selecting, shaping, and/or sizing a synthetic element to fit the determined probe imaging area.

Augmented image 400-1 illustrates one example of a synthetic element that includes a border element outlining a probe imaging area as depicted in an image of an anatomical scene. As shown, the synthetic element may allow at least part of the probe imaging area (e.g., region 406), as depicted in the visual image captured by the first imaging modality, to remain visible in augmented image 400-1 (e.g., by not substantially occluding the probe imaging area from view). Additional or alternative synthetic elements may be used to augment the visual image in other examples. As an example, another version of synthetic element 402 may include additional content presented within the border element.

Figure 4B:
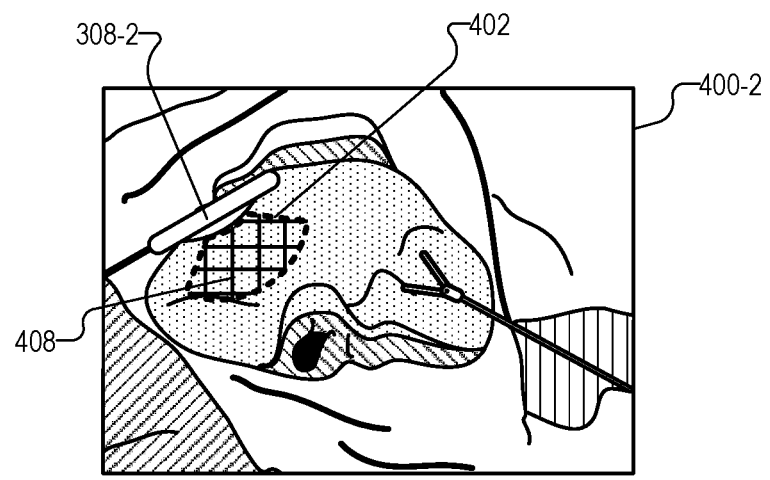

FIG. 4B depicts an illustrative augmented image 400-2 that is similar to augmented image 400-1 and further includes spatial markers 408 positioned relative to the probe imaging area. As shown, synthetic element 402 may include a border element (e.g., as shown by dashed segments) outlining, within the visual image, a boundary of the area of the anatomical scene being imaged by imaging probe 308-2, and spatial markers 408 positioned within the border element and thus within the area of the anatomical scene being imaged by imaging probe 308-2. Spatial markers 408 may include any supplemental synthetic features within synthetic element 402. Spatial markers 408 may be configured to visually indicate an area or space being imaged by a probe and/or any information about or associated with the area or space being imaged by the probe. In certain examples, for instance, spatial markers 408 may include any synthetic markers added to the visual image of the anatomical scene and that visually indicate information about the probe imaging area, such as a position of an area or space of the probe imaging area, an orientation of the probe imaging area, depths being imaged, and/or locations within the probe imaging area. A presentation of spatial markers 408 relative to the probe imaging area as depicted in the visual image captured by the first imaging modality may assist a user in identifying the area or space being imaged by a probe and/or information about that probe imaging area, such as specific locations within the probe imaging area and/or specific anatomical features and spatial relationships between spatial markers 408 and the anatomical features.

In the example illustrated in FIG. 4B, spatial markers 408 include grid lines formed by horizontal and vertical lines. The positioning of the grid lines relative to the probe imaging area indicates specific locations relative to anatomical features within the probe imaging area. Additional or alternative spatial markers may be used in other examples. For instance, spatial markers may include point markers (e.g., a grid of points), depth markers (e.g., depth lines of concentric arcs), patterns of markers, shading markers, and/or any other suitable synthetic features within synthetic element 402, such as synthetic markers referencing location and/or distance within the probe imaging area.

Figure 4C:
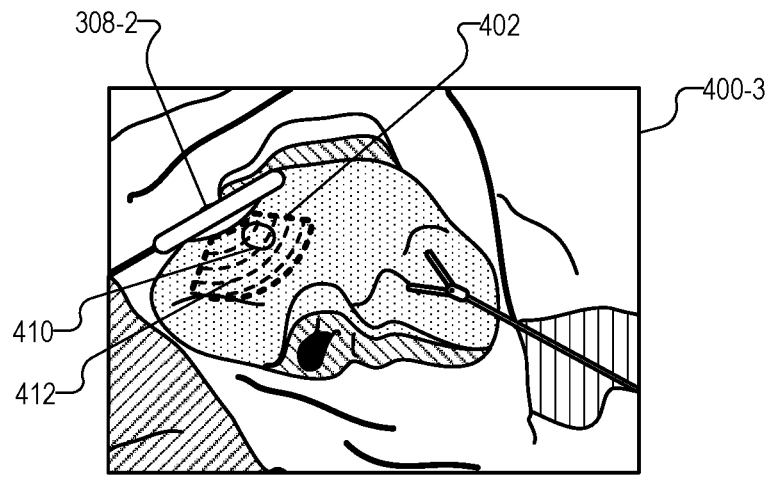

FIG. 4C depicts an illustrative augmented image 400-3 that is similar to augmented image 400-1 and further includes a highlight element 410 and depth lines 412 positioned within a border element of synthetic element 402. Highlight element 410 may include any graphical element that highlights or otherwise visually identifies a select portion of the probe imaging area. As shown, highlight element 410 may include a generally oval-shaped spatial marker positioned relative to the probe imaging area. Highlight element 410 may include any other marker or set of markers configured to highlight a select portion of the probe imaging area within synthetic element 410. Highlight element 410 may be represented by different shapes, different lines, different areas of color, other suitable representations, and/or different combinations of visual representations. Depth lines 412 are depicted as concentric arcs and illustrate another example of spatial markers. Depth lines 412 may provide location context for highlight element 410 within the border element of synthetic element 402. Additionally or alternatively, other suitable spatial markers may be provided together with highlight element 410 within the border element of synthetic element 402.

System 100 may place highlight element 410 based on any suitable information about the anatomical scene. For example, system 100 may be configured to identify a particular feature of the anatomical scene depicted in the visual image and place highlight element 410 relative to the feature to visually identify the feature. Additionally or alternatively, system 100 may place highlight element 410 relative to the visual image based on user input such as user input configured to move highlight element 410 relative to the visual image.

Figure 4D:
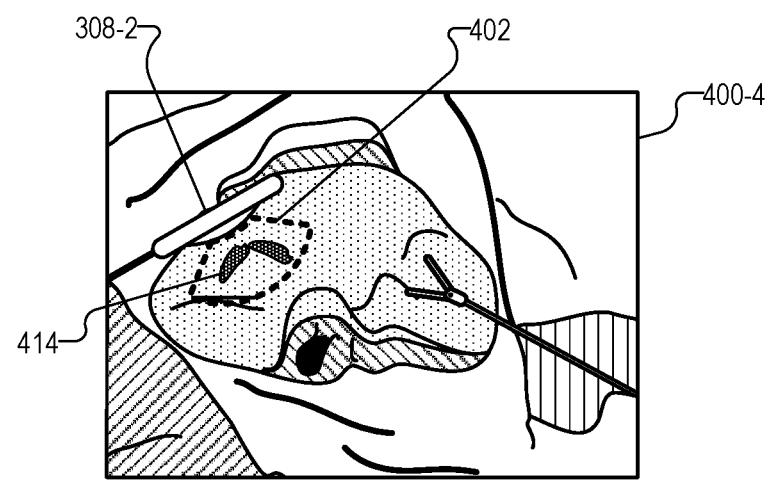

FIG. 4D depicts an illustrative augmented image 400-4 that is similar to augmented image 400-1 and further includes a select portion 414 of a probe image positioned within a border element of synthetic element 402. The select portion 414 of the probe image may be a specific portion of a probe image captured by the imaging probe. System 100 may select the select portion 414 for use in augmenting the visual image based on any suitable information about the anatomical scene. For example, system 100 may be configured to identify a particular feature of the anatomical scene depicted in the probe image and select a portion of the probe image that depicts the feature for placement within the border element of synthetic element 402. System 100 may position the select portion 414 of the probe image to represent a correlation between the feature and a location in the probe imaging area. Additionally or alternatively, system 100 may place select and place the select portion 414 of the probe image based on user input such as user input configured to move indicate a desired select portion of the probe image.

In some examples, the imaging probe may be an ultrasound probe, and the select portion 414 of the probe image may be a Doppler image portion of the probe image. The Doppler image portion may advantageously show blood flow locations relative to the visual indication of the probe imaging area while leaving at least a portion of the probe imaging area, as captured by the first imaging modality and depicted in the visual image, unoccluded from view by a user.

System 100 may integrate the select portion 414 with the depiction of the probe imaging area as captured by the first imaging modality in any suitable way. For example, the representation of the select portion 414 of the probe image may be overlaid on the imagery of the anatomical scene captured by the first imaging modality in a partially transparent manner. Various display features (e.g., color schemes) may be used to display the select portion 414 within the border element of synthetic element 402. Although not shown, suitable spatial markers (e.g., grid lines) may also be presented together with the select portion 414 of the probe image within the border element of synthetic element 402.

FIGS. 4A-4D illustrate examples of augmentations that visually indicate a probe imaging area as depicted in a captured image of an anatomical scene. Some of the augmentations also indicate additional information about the probe imaging area and/or in relation to the probe imaging area. The examples are illustrative. Additional or alternative augmentations that indicate the probe imaging area and/or information about the probe imaging area may be used in other examples.

System 100 may be configured to further augment a visual image of an anatomical scene with probe imagery captured by the imaging probe. The probe imagery may include at least part of a probe image, and system 100 may place the probe image to not overlap the probe imaging area as depicted in the visual image. In certain examples, system 100 may be configured to present the visual image augmented only with a probe image and not with an additional synthetic element such as synthetic element 402. In other examples, system 100 may be configured to augment the visual image with both a synthetic element that indicates the probe imaging area (e.g., synthetic element 402) and with a probe image captured by the imaging probe. In augmented images that include both a synthetic element indicating a probe imaging area and a probe image, the probe image may be positioned not to overlap the synthetic element or the depiction of the probe imaging area. The probe image may not overlap the synthetic element or the depiction of the probe imaging area by the probe image being positioned in an augmented image such that no part of the probe image is positioned within the probe imaging area or an area visually indicated by the synthetic element.

Figure 5A:
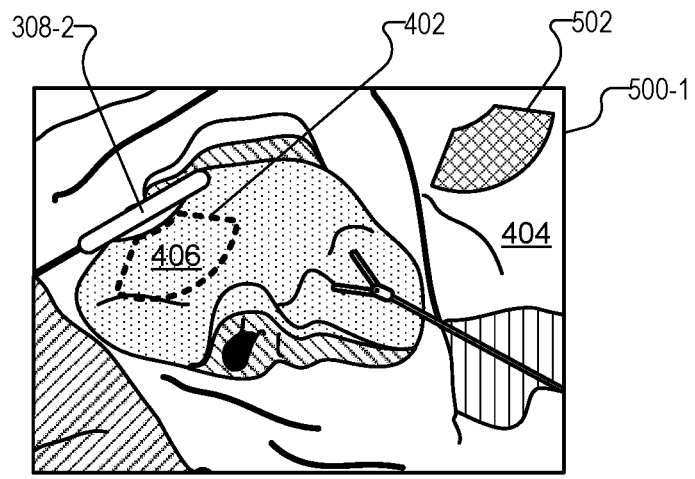

FIG. 5A depicts an illustrative augmented image 500-1 that is similar to augmented image 400-1 and further includes a probe image 502 within first region 404. As shown, probe image 502 is positioned outside of synthetic element 402. For example, probe image 502 is placed at a location within augmented image 500-1 that does not overlap a depiction of an area of the anatomical scene being imaged by the imaging probe (i.e., the probe imaging area represented by second region 406 indicated by synthetic element 402). For example, probe image 502 may be presented in a corner area of augmented image 500-1 to avoid occluding a view of the probe imaging area as indicated by synthetic element 402. Probe image 502 may be placed at any other suitable position in other examples, including any suitable position within, outside of, or partially within and partially outside of the visual image captured by the first imaging modality. In certain examples, the position of the probe image 502 relative to the visual image captured by the first imaging modality may be selected based on user input suitable to select the position of probe image 502 within augmented image 500-1.

In FIG. 5A, a representation of the anatomical scene within synthetic element 402 is illustrated with a dot pattern that represents the anatomical scene as captured by the first imaging modality (e.g., endoscopic imaging), and a representation of probe image 502 is illustrated with a diagonally-crossed line pattern that represents a probe image captured by a second imaging modality (e.g., ultrasound imaging) that is different from the first imaging modality. A medical team member viewing augmented image 500-1 may concurrently view visualizations of portions of the anatomical scene as captured by different imaging modalities. Because the representation of probe image 502 does not overlap synthetic element 402 or second region 406, the medical team member may view the anatomical scene as captured by the different imaging modalities while having a substantially unoccluded view of the depiction of the probe imaging area of the anatomical scene as captured by a first imaging modality within second region 406 where viewing clarity may be desired for a medical procedure.

While in certain examples probe image 502 may include an ultrasound image, any other suitable imagery captured by another imaging modality may be used to augment the visual image captured by the first imaging modality. For example, system 100 may determine a slice of a 3D model (e.g., a 3D model generated from OCT or REIMS) based on a position of synthetic element 402 relative to the anatomical scene and use an image of the slice to augment the visual image captured by the first imaging modality. Accordingly, in augmented image 500-1, probe image 502 may be replaced with an image captured by any suitable second imaging modality. In certain examples, an image that is used to augment the visual image may be selected by way of user input to a computer-assisted medical system. For example, a user of the computer-assisted medical system may provide input to toggle from one imaging modality image being projected onto the corner region to another imaging modality image being projected onto the corner region (e.g., from an ultrasound image to an OCT or REIMS model image or vice versa).

Augmented image 500-1 illustrates one example of an augmentation of a visual image of an anatomical scene as captured by a first imaging modality with an image of the anatomical scene as captured by a second imaging modality. Additional or alternative augmentation content may be included in other examples. For example, system 100 may further augment the visual image with content associated with the image captured by the second imaging modality, such as by presenting synthetic elements in association with probe image 502.

Figure 5B:
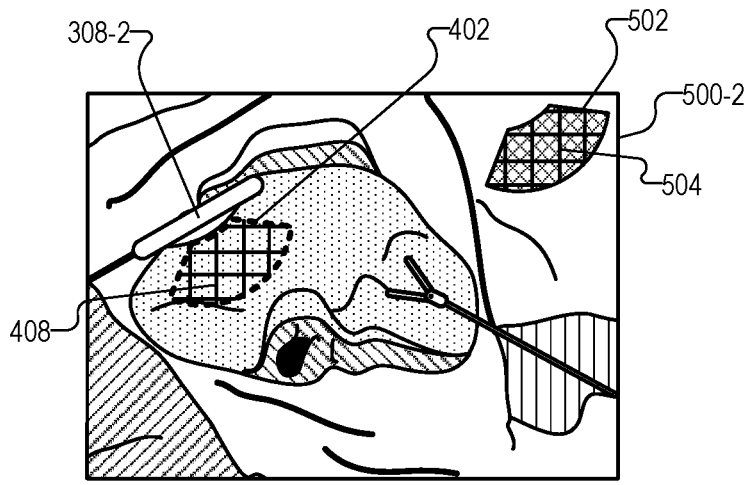

FIG. 5B depicts an illustrative augmented image 500-2 that is similar to augmented image 500-1 and further includes spatial markers 408 positioned within a border element of synthetic element 402 and spatial markers 504 positioned within a border of probe image 502. Spatial markers 504 may be any synthetic markers that visually indicate information about specific locations within the probe image 502. For example, spatial markers 504 may include synthetic elements positioned to indicate specific locations within the probe image 502. By presenting spatial markers 504 relative to the probe image as captured by the imaging probe, the spatial markers 504 may assist a user in identifying specific locations within the probe image 502, such as specific anatomical features (e.g., subsurface anatomy features captured by an ultrasound probe) and spatial relationships between spatial markers 504 and the anatomical features.

Spatial markers 504 within probe image 502 may correspond to spatial markers 408 within synthetic element 402 and may aid a medical team member viewing augmented image 500-2 to mentally align the separately-presented imagery (e.g., imagery of the probe imaging area captured by a first imaging modality and probe imagery captured by a second imaging modality) of the anatomical scene. To this end, a specific spatial marker 408 (an intersection of particular grid lines) may indicate a specific location within the probe imaging area as depicted in a visual image captured by the first imaging modality, and a corresponding spatial marker 504 (a corresponding intersection of particular grid lines) may indicate a specific location within the probe image captured by the imaging probe to indicate a relationship between the specific location within the probe imaging area and the specific location within the probe image. Spatial markers 504 may be any suitable markers referencing location and/or distance within the probe image.

Figure 5C:
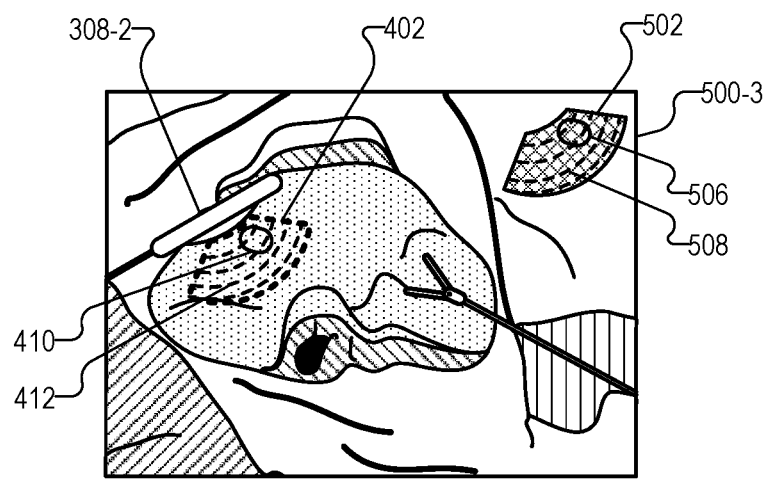

FIG. 5C depicts an illustrative augmented image 500-3 that is similar to augmented image 500-1 and further includes highlight element 410 and depth lines 412 positioned within synthetic element 402 and a corresponding highlight element 506 and depth lines 508 positioned within probe image 502. Highlight element 410 and depth lines 412 are described above. Highlight element 506 may include any graphical element that highlights or otherwise visually identifies a select portion of the probe image 502. As shown, highlight element 506 may include a generally oval-shaped spatial marker positioned relative to the probe image 502. Highlight element 506 may include any other marker or set of markers configured to highlight a select portion of the probe image 502. Highlight element 506 may be represented by different shapes, different lines, different areas of color, other suitable representations, and/or different combinations of visual representations. Depth lines 508 are depicted as concentric arcs and illustrate another example of spatial markers. Depth lines 508 may provide location context for highlight element 506. Additionally or alternatively, other suitable spatial markers may be provided together with highlight element 506 within probe image 502. By presenting highlight element 506 and/or depth lines 508 relative to the probe image as captured by the imaging probe, the highlight element 506 and/or depth lines 508 may assist a user in identifying specific locations within the probe image 502, such as specific anatomical features (e.g., subsurface anatomy features captured by an ultrasound probe) and spatial relationships between highlight element 506 or depth lines 508 and the anatomical features.

System 100 may place highlight element 506 based on any suitable information about the probe image. For example, system 100 may be configured to identify a particular feature depicted in the probe image and place highlight element 506 relative to the feature to visually identify the feature. Additionally or alternatively, system 100 may place highlight element 506 relative to the visual image based on user input such as user input configured to move highlight element 506 relative to the visual image.

Highlight element 506 within probe image 502 may correspond to highlight element 410 within synthetic element 402 and may aid a medical team member viewing augmented image 500-3 to mentally align the separately-presented imagery (e.g., imagery of the probe imaging area captured by a first imaging modality and probe imagery captured by a second imaging modality) of the anatomical scene. To this end, highlight element 410 may indicate a specific location within the probe imaging area as depicted in a visual image captured by the first imaging modality, and corresponding highlight element 506 may indicate a specific location within the probe image 502 captured by the imaging probe to indicate a relationship between the specific location within the probe imaging area and the specific location within the probe image. Similarly, depth lines 508 within probe image 502 may correspond to depth lines 412 within synthetic element 402 and may aid a medical team member viewing augmented image 500-3 to mentally align the separately-presented imagery of the anatomical scene.

Figure 5D:
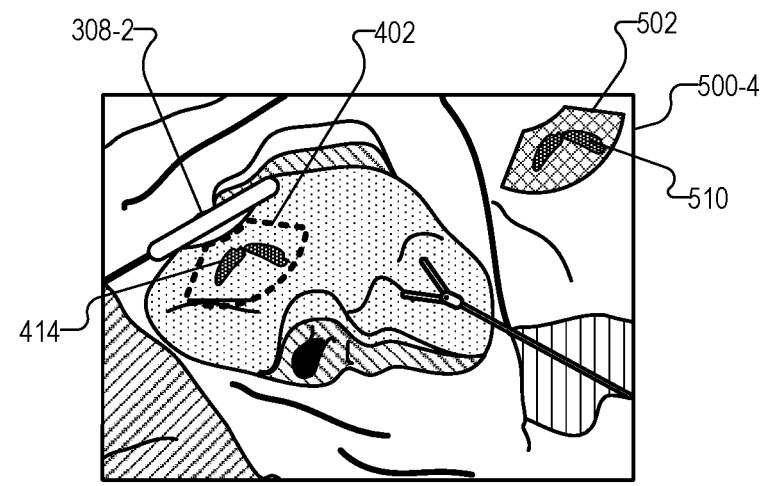

FIG. 5D depicts an illustrative augmented image 500-4 that is similar to augmented image 500-1 and further includes a select portion 510 of probe image 502 represented as select portion 414 within synthetic element 402. In some examples, select portion 510 of the probe image 502 may be a Doppler image portion of the probe image 502. Select portion 510 may be integrated with the depiction of probe image 502. Various color schemes may be suitable to display select portion 510 within probe image 502. A representation of select portion 510 of probe image 502 may also be presented as select portion 414 within synthetic element 402, as shown, to provide a visual correlation between the probe image 502 and the probe imaging area as depicted in the visual image captured by the first imaging modality. To this end, select portion 414 may indicate a specific location within the probe imaging area as depicted in the visual image captured by the first imaging modality, and corresponding select portion 510 may indicate a specific location within the probe image 502 captured by the imaging probe to indicate a relationship between the specific location within the probe imaging area and the specific location within the probe image. Although not shown, suitable spatial markers may also be provided together with select portion 510 of probe image 502. Correlated spatial markers may also be provided together with select portion 414 displayed within synthetic element 402. In certain examples, probe image 502 may be a full regular probe image captured by the imaging probe, and select portion 414 may be a Doppler image captured by the imaging probe.

While a Doppler image portion of a probe image is illustrated as a select portion 414 of the probe image in FIG. 5D, additional or alternative select portions of a probe image may be selected and displaying within synthetic element 402 in other examples. For example, system 100 may be configured to identify, based on probe image, an anatomical feature (e.g., a tumor) depicted in the probe image and to select a portion of the probe image representing the anatomical feature for display within synthetic element 402. System 100 may be configured to identify an anatomical feature depicted in a probe image in any suitable way.

Other examples of augmented images of an anatomical scene may include a visual image of the anatomical scene augmented with a preview placeholder indicating a display position for a probe image to be captured by the imaging probe. Examples of such augmented images will now be described with reference to FIGS. 6A-6B and 7A-7B.

Figure 6A:
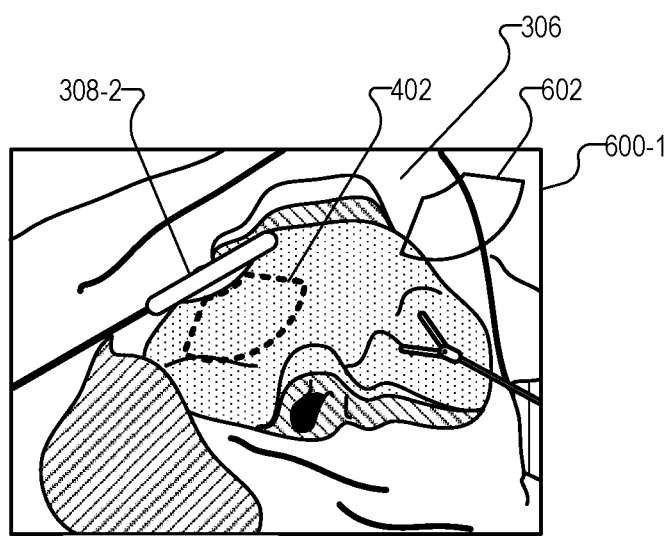
Figure 6B:
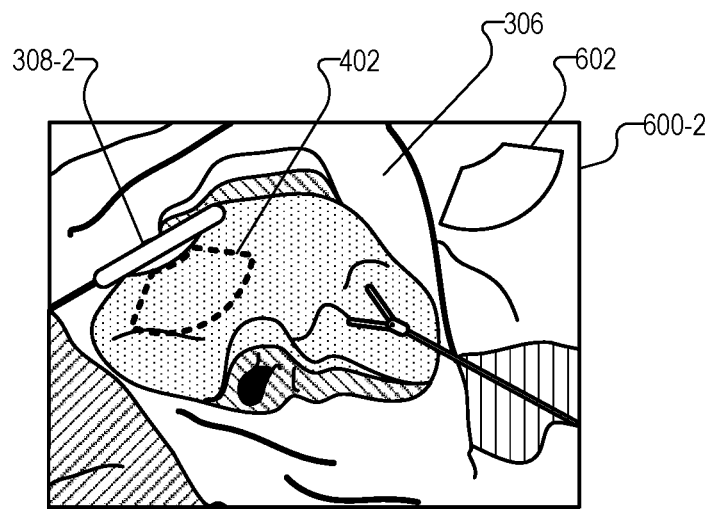

FIG. 6A illustrates an augmented image 600-1 of the anatomical scene of FIG. 3A. As shown, a visual image of the anatomical scene may be augmented with synthetic element 402 and a preview placeholder 602 indicating a display position for a probe image yet to be captured. As shown in augmented image 600-1 of FIG. 6A, preview placeholder 602 is placed over a portion of anatomy 306. Presentation of preview placeholder 602 may indicate to a medical team member that if a probe image is displayed at the same location at which preview placeholder 602 is displayed, the probe image may occlude from view that portion of anatomy 306. Advantageously, based on this indication, the medical team member may make an adjustment to cause that portion of anatomy 306 not to be occluded by the probe image. For example, an image render viewpoint for the visual image may be adjusted (e.g., by repositioning a first imaging modality instrument, such as an endoscope) to cause anatomy 306 to be repositioned within the visual image in a manner that causes that portion of anatomy 306 to be moved away from the preview placeholder 602 to form an arrangement that is more desirable to the medical team member. FIG. 6B illustrates an augmented image 600-2 that is similar to augmented image 600-2 but with the anatomy 306 shifted within the image frame to move that portion of anatomy 306 away from the preview placeholder 602 such that a probe image displayed at the same location of the preview placeholder 602 would not occlude that portion of anatomy 306.

Figure 7A:
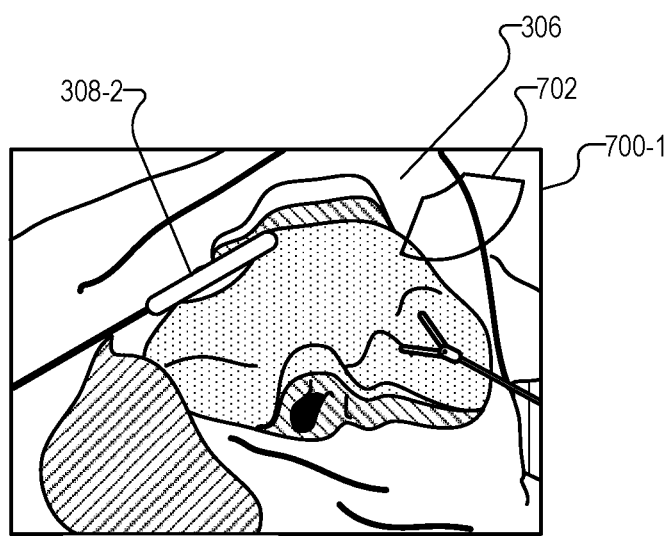
Figure 7B:
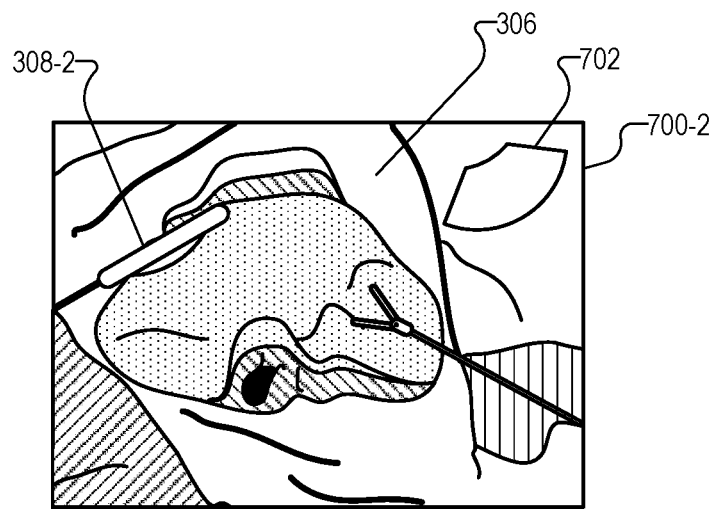

In augmented images 600-1 and 600-2, the preview placeholder 602 is displayed together with synthetic element 402. In other examples, a preview placeholder may be displayed without synthetic element 402 or any other augmentations. For example, FIGS. 7A and 7B illustrate augmented images 700-1 and 700-2 that are similar to augmented images 600-1 and 600-2, respectively, but do not include synthetic element 402.

System 100 may be configured to augment, in any of the ways described herein, a visual image of an anatomical scene at any suitable time and/or in response to any suitable event. For example, system 100 may augment the visual image in response to an occurrence of a predefined event.

In certain examples, a predefined event may include an imaging probe having a stationary state for a threshold amount of time. In such examples system 100 may be configured to detect that the imaging probe is in a stationary state for a threshold amount of time and, in response, augment the visual image in any of the ways described herein.

The stationary state may be defined in any suitable way. As an example, a stationary state may include a state in which the imaging probe remains at a pose that does not change more than a defined rate or tolerance amount. Accordingly, the stationary state may be defined to include movement up to an allowed rate or tolerance amount and to exclude movement exceeding the allowed rate or tolerance amount. The allowed rate or tolerance rate may be defined based on capabilities of the imaging probe and/or system capabilities for processing images captured by the imaging probe.

By allowing an augmentation to be performed only when the imaging probe is in a stationary state, the augmentation may be controlled such that the augmentation is provided only when meaningful or enhanced data is available. To illustrate, when the imaging probe is being moved within the anatomical scene at a rate that exceeds a threshold, system capabilities may not be able to process probe imagery fast enough to provide meaningful or enhanced probe imagery for display in an augmentation such as probe image 502 shown in FIGS. 5A-5D. Accordingly, system 100 may be configured to abstain from augmenting a visual image with a probe image when the imaging probe is being moved at a rate that exceeds a threshold. Instead of providing a probe image as an augmentation, system 100 may provide no augmentation or may provide only a different augmentation such as synthetic element 402 and/or preview placeholder 602 or 702. In response to the probe image being in a stationary state, system 100 may provide an augmentation such as preview placeholder 602 or 702, probe image 502, synthetic element 402, and/or any other augmentation. This may allow a surgical team member to put the imaging probe in a stationary state to trigger an augmentation of the visual image that may help the surgical team member determine and/or perform next steps of a medical procedure. In some examples, the stationary state of the imaging probe may allow for enhanced probe imaging and/or more accurate detection of pose of the imaging probe.

In certain examples, a predefined event may include the imaging probe contacting tissue at the anatomical scene. Tissue contact by the imaging probe may be detected in any suitable way. System 100 may be configured to detect that the imaging probe is in contact with tissue and, in response, augment a visual image of an anatomical scene in any of the ways described herein.

In certain examples, a predefined event may include reception of predefined user input provided by a surgical team member, such as user input provided to a computer-assisted medical system. System 100 may be configured to detect reception of predefined user input and, in response, augment a visual image of an anatomical scene in any of the ways described herein. In certain examples, specific user inputs may be mapped to respective augmentations such that reception of a specific user input trigger a specific augmentation. For example, system 100 may detect reception of a specific user input and, in response, may augment a visual image of an anatomical scene with a select portion 414 and/or 510 of a probe image captured by an imaging probe at the anatomical scene.

In certain examples, a predefined event may include a determination by system 100 that a medical team member intends to interact with or use the imaging probe. System 100 may be configured to determine that the medical team member intends to interact with or use the imaging probe in any suitable way and based on any information about the imaging probe and/or a computer-assisted medical system and/or events of a medical procedure. For example, system 100 may detect, based on such information, an intent of the surgical team member to use a medical instrument to grasp or otherwise engage a drop-in imaging probe (e.g., by detecting movement of the medical instrument toward the imaging probe) or an actual grasping or other engagement of the imaging probe with the medical instrument. In response, system 100 may provide information about the imaging probe. For example, system 100 may augment a visual image of the anatomical scene in any of the ways described herein. For example, system 100 may augment the visual image with a preview placeholder indicating a display position of a probe image to be captured by the imaging probe.

As mentioned, system 100 may be implemented in or communicatively coupled to a computer-assisted medical system. System 100 may receive input from and provide output to the computer-assisted medical system. For example, system 100 may access imagery of an anatomical scene and/or any information about the anatomical scene and/or the computer-assisted medical system from the computer-assisted medical system, use the accessed imagery and/or information to perform any of the processing described herein to generate augmented imagery of the anatomical scene, and provide data representative of the augmented imagery to the computer-assisted medical system for display (e.g., by a display device associated with the computer-assisted medical system).

Figure 8:
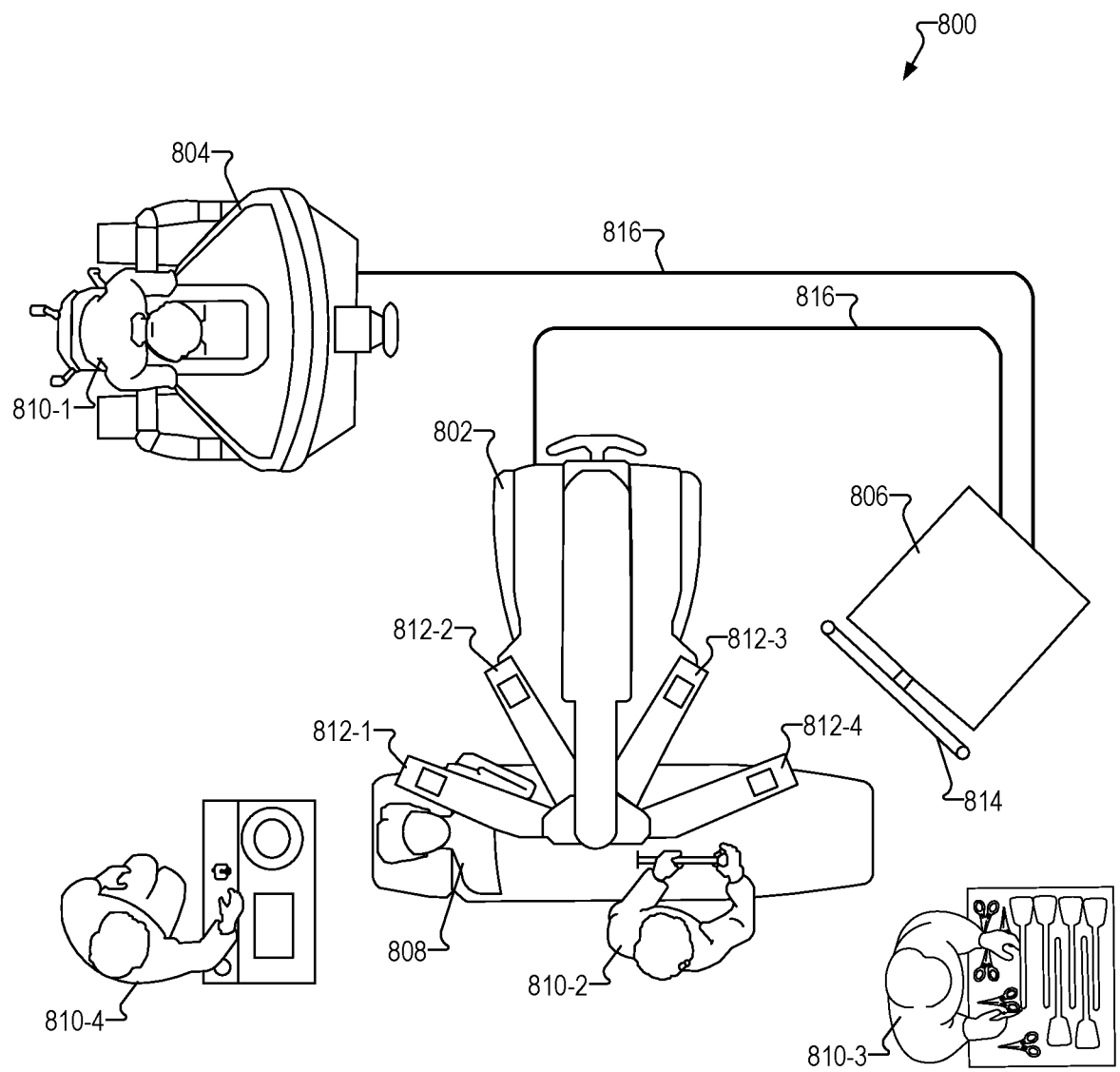
FIG. 8 depicts an illustrative computer-assisted medical system according to principles described herein.

FIG. 8 depicts an illustrative computer-assisted medical system 800 ("medical system 800"). System 100 may be implemented by medical system 800, connected to medical system 800, and/or otherwise used in conjunction with medical system 800.

As shown, medical system 800 may include a manipulating system 802, a user control system 804, and an auxiliary system 806 communicatively coupled one to another. Medical system 800 may be utilized by a medical team to perform a computer-assisted medical procedure on a patient 808. As shown, the medical team may include a medical team member 810-1, an assistant 810-2, a nurse 810-3, and an anesthesiologist 810-4, all of whom may be collectively referred to as "medical team members 810." Additional or alternative medical team members may be present during a medical session as may serve a particular implementation.

While FIG. 8 depicts an ongoing minimally invasive medical procedure, it will be understood that medical system 800 may similarly be used to perform open medical procedures or other types of medical procedures that may similarly benefit from the accuracy and convenience of medical system 800. Additionally, it will be understood that the medical session throughout which medical system 800 may be employed may not only include an operative phase of a medical procedure, as is illustrated in FIG. 8, but may also include preoperative, postoperative, and/or other suitable phases of the medical procedure.

As shown in FIG. 8, manipulating system 802 may include a plurality of manipulator arms 812 (e.g., manipulator arms 812-1 through 812-4) to which a plurality of medical instruments may be coupled. Each medical instrument may be implemented by any suitable medical tool (e.g., a tool having tissue-interaction functions), surgical tool, imaging device (e.g., an endoscope, an ultrasound tool, etc.), sensing instrument (e.g., a force-sensing medical instrument), diagnostic instrument, or the like that may be used for a computer-assisted medical procedure on patient 808 (e.g., by being at least partially inserted into patient 808 and manipulated to perform a computer-assisted medical procedure on patient 808). While manipulating system 802 is depicted and described herein as including four manipulator arms 812, it will be recognized that manipulating system 802 may include only a single manipulator arm 812 or any other number of manipulator arms as may serve a particular implementation.

Manipulator arms 812 and/or medical instruments attached to manipulator arms 812 may include one or more displacement transducers, orientational sensors, and/or positional sensors used to generate raw (i.e., uncorrected) kinematics information. One or more components of medical system 800 may be configured to use the kinematics information to track (e.g., determine positions of) and/or control the medical instruments. System 100 may be configured to access and use the kinematics information for one or more augmentation operations, such as to track a pose of an imaging probe (e.g., by tracking a pose of a medical instrument grasping or otherwise engaging the imaging probe at an anatomical scene).

User control system 804 may be configured to facilitate control by medical team member 810-1 of manipulator arms 812 and medical instruments attached to manipulator arms 812. For example, medical team member 810-1 may interact with user control system 804 to remotely move or manipulate manipulator arms 812 and the medical instruments. To this end, user control system 804 may provide medical team member 810-1 with imagery (e.g., high-definition 3D imagery) of an anatomical scene associated with patient 808 as captured by an imaging system (e.g., any of the medical imaging systems described herein). In certain examples, user control system 804 may include a stereo viewer having two displays where stereoscopic images of an anatomical scene associated with patient 808 and generated by a stereoscopic imaging system may be viewed by medical team member 810-1. In certain examples, augmented imagery generated by system 100 may be displayed by user control system 804. Medical team member 810-1 may utilize the imagery displayed by user control system 804 to perform one or more procedures with one or more medical instruments attached to manipulator arms 812.

To facilitate control of medical instruments, user control system 804 may include a set of master controls. The master controls may be manipulated by medical team member 810-1 to control movement of medical instruments (e.g., by utilizing robotic and/or teleoperation technology). The master controls may be configured to detect a wide variety of hand, wrist, and finger movements by medical team member 810-1. In this manner, medical team member 810-1 may intuitively perform a procedure using one or more medical instruments.

Auxiliary system 806 may include one or more computing devices configured to perform primary processing operations of medical system 800. In such configurations, the one or more computing devices included in auxiliary system 806 may control and/or coordinate operations performed by various other components (e.g., manipulating system 802 and user control system 804) of medical system 800. For example, a computing device included in user control system 804 may transmit instructions to manipulating system 802 by way of the one or more computing devices included in auxiliary system 806. As another example, auxiliary system 806 may receive, from manipulating system 802, and process image data representative of imagery captured by an imaging device attached to one of manipulator arms 812.

In some examples, auxiliary system 806 may be configured to present visual content to medical team members 810 who may not have access to the images provided to medical team member 810-1 at user control system 804. To this end, auxiliary system 806 may include a display monitor 814 configured to display one or more user interfaces, such as images (e.g., 2D images) of the anatomical scene, information associated with patient 808 and/or the medical procedure, and/or any other visual content as may serve a particular implementation. For example, display monitor 814 may display images of the anatomical scene together with additional content (e.g., graphical content, contextual information, etc.) concurrently displayed with the images. System 100 may be configured to provide augmented images generated by system 100 to display monitor 814 for display. In some embodiments, display monitor 814 is implemented by a touchscreen display with which medical team members 810 may interact (e.g., by way of touch gestures) to provide user input to medical system 800.

Manipulating system 802, user control system 804, and auxiliary system 806 may be communicatively coupled one to another in any suitable manner. For example, as shown in FIG. 8, manipulating system 802, user control system 804, and auxiliary system 806 may be communicatively coupled by way of control lines 816, which may represent any wired or wireless communication link as may serve a particular implementation. To this end, manipulating system 802, user control system 804, and auxiliary system 806 may each include one or more wired or wireless communication interfaces, such as one or more local area network interfaces, Wi-Fi network interfaces, cellular interfaces, etc.

Computer-assisted medical system 800 illustrates one example of a computer-assisted medical system which system 100 may be part of and/or with which system 100 may interact with to provide augmented imagery of an anatomical scene as described herein. System 100 may be implemented by, in communication with, and/or operate in conjunction with any other suitable medical system (e.g., a surgical system, a robotic system, etc.).

Figure 9:
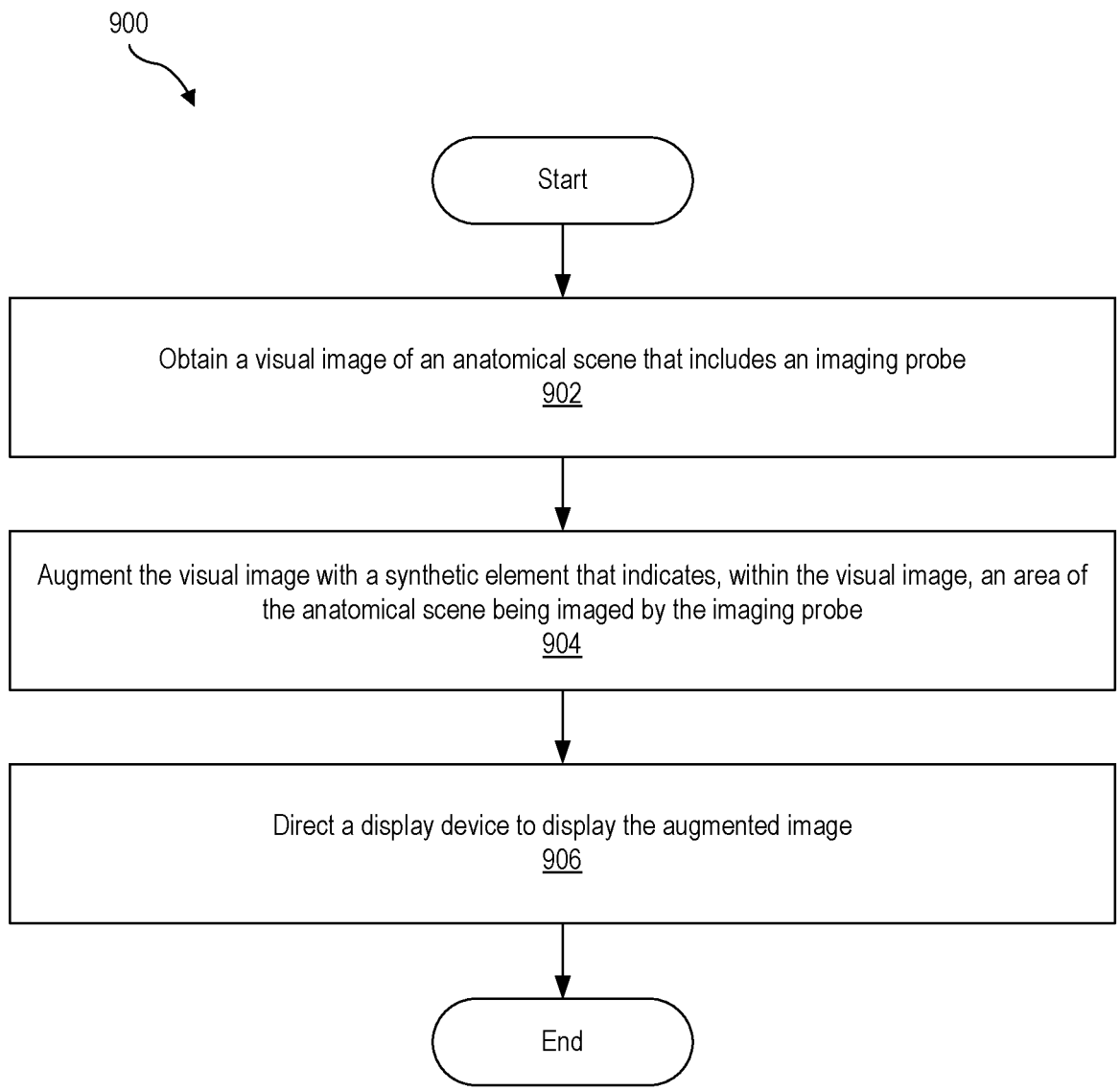
FIGS. 9-11 depict illustrative methods according to principles described herein.

FIG. 9 shows an illustrative method 900. While FIG. 9 depicts illustrative operations according to one embodiment, other embodiments may omit, add to, reorder, combine, and/or modify any of the steps shown in FIG. 9 One or more of the operations shown in in FIG. 9 may be performed by a computing system such as system 100, any components included therein, and/or any implementation thereof.

In operation 902, a computing system obtains a visual image of an anatomical scene that includes an imaging probe. The visual image may be captured by a first imaging modality (e.g., an endoscope), and the computing system may obtain the visual image from the first imaging modality or any other suitable source. Operation 902 may be performed in any of the ways described herein.

In operation 904, the computing system augments the visual image with a synthetic element that indicates, within the visual image, an area of the anatomical scene being imaged by the imaging probe. The synthetic element may include one or more of the illustrative synthetic elements described herein, such as synthetic element 402 and/or preview placeholder 602 or 702. In certain implementations, for example, the synthetic element may indicate a boundary of the area of the anatomical scene being imaged by the imaging probe and may include spatial markers such as spatial markers 408 and/or 504, highlight element 410 and/or 506, depth lines 412 and/or 508, or any suitable combination or sub-combination thereof within the boundary and thus within the area of the anatomical scene being imaged by the imaging probe. In certain examples, a synthetic element may indicate the area of the anatomical scene being imaged by the imaging probe without explicitly indicating the boundary of the area and including spatial markers within the area that may implicitly indicate the area. For example, a synthetic element may include a light speckle as spatial elements within the area being imaged without a hard boundary line. Operation 904 may be performed in any of the ways described herein.

In operation 906, the computing system directs a display device to display the augmented image. To this end, the computing system may provide data representative of the augmented image to the display device for processing and display of the augmented image by the display device. Operation 906 may be performed in any of the ways described herein.

Figure 10:
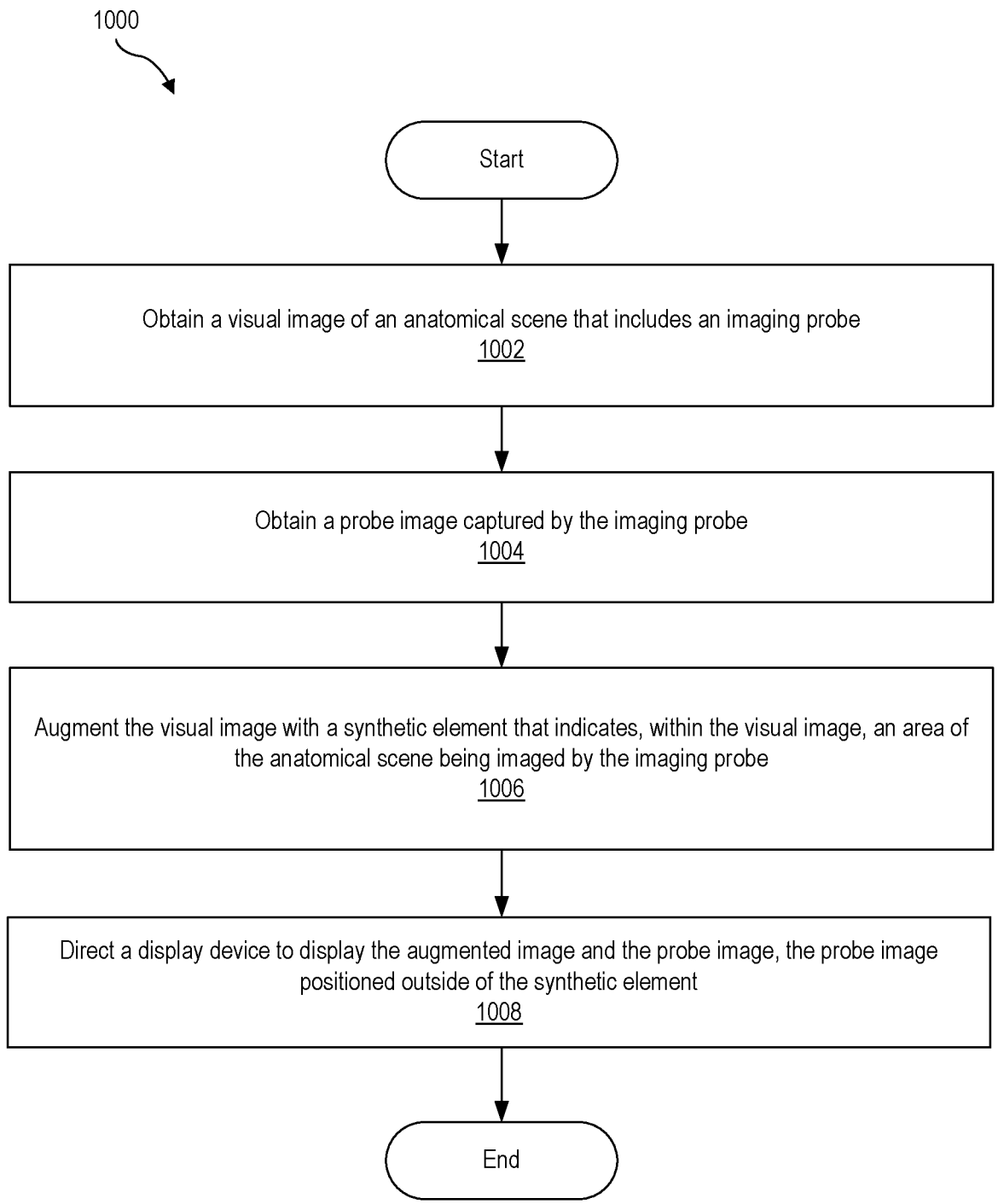

FIG. 10 shows an illustrative method 1000. While FIG. 10 depicts illustrative operations according to one embodiment, other embodiments may omit, add to, reorder, combine, and/or modify any of the steps shown in FIG. 10 One or more of the operations shown in in FIG. 10 may be performed by a computing system such as system 100, any components included therein, and/or any implementation thereof.

In operation 1002, a computing system obtains a visual image of an anatomical scene that includes an imaging probe. The visual image may be captured by a first imaging modality (e.g., an endoscope), and the computing system may obtain the visual image from the first imaging modality or any other suitable source. Operation 1002 may be performed in any of the ways described herein.

In operation 1004, the computing system obtains a probe image captured by the imaging probe. The imaging probe may be or provide a second imaging modality, and the computing system may obtain the probe image from the second imaging modality or any other suitable source. Operation 1004 may be performed in any of the ways described herein.

In operation 1006, the computing system augments the visual image with a synthetic element that indicates, within the visual image, an area of the anatomical scene being imaged by the imaging probe. Operation 1006 may be performed in any of the ways described herein.

In operation 1008, the computing system directs a display device to display the augmented image and the probe image such that the probe image is positioned outside of the synthetic element such that the probe image does not overlap a depiction, in the visual image, of the area of the anatomical scene being imaged by the imaging probe. For example, the computing system may provide, for display, an image such as any of the images shown in FIGS. 5A-5D. To this end, the computing system may provide data representative of the image to the display device for processing and display of the image by the display device. Operation 1008 may be performed in any of the ways described herein.

Figure 11:
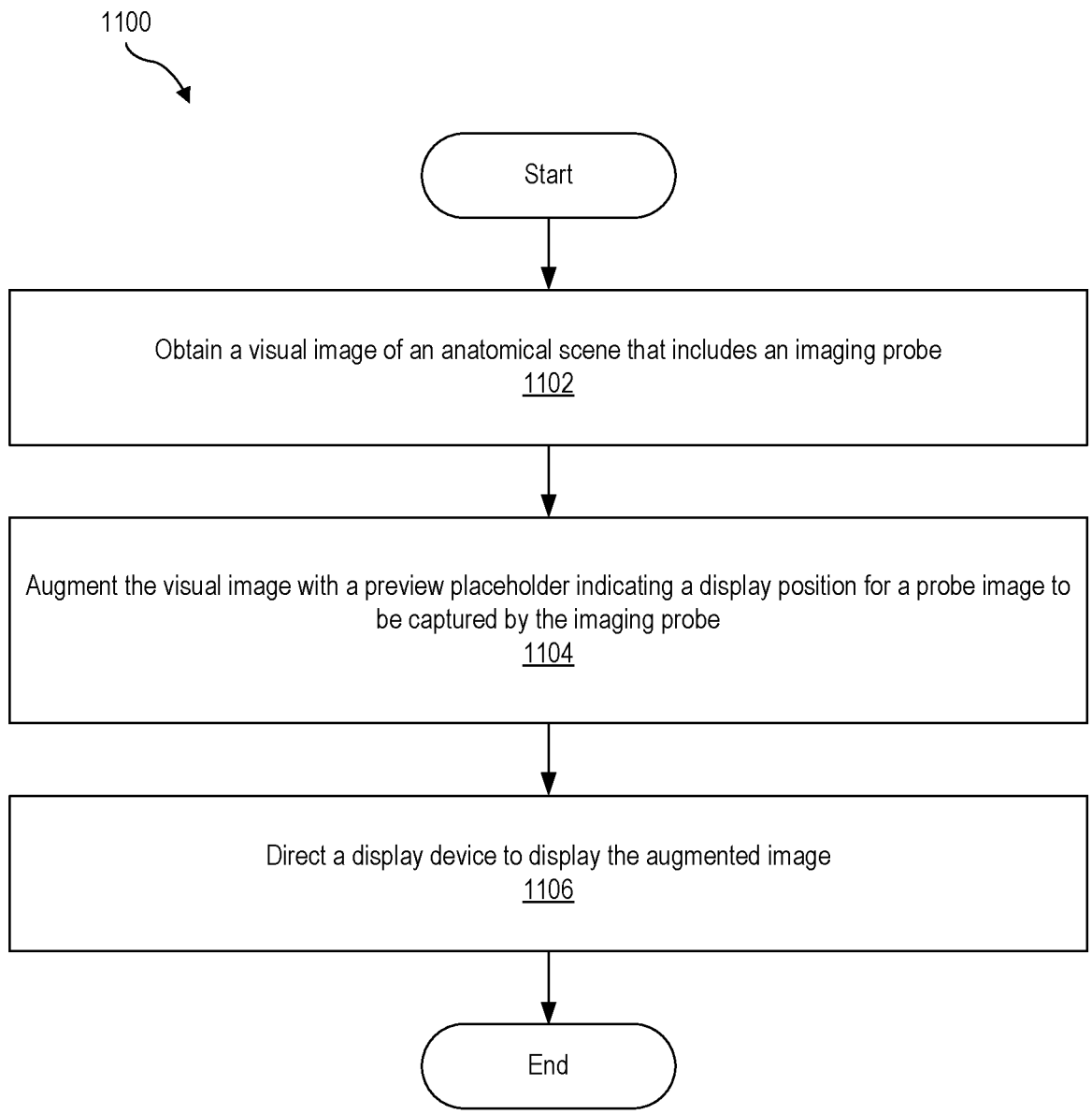

FIG. 11 shows an illustrative method 1100. While FIG. 11 depicts illustrative operations according to one embodiment, other embodiments may omit, add to, reorder, combine, and/or modify any of the steps shown in FIG. 11 One or more of the operations shown in in FIG. 11 may be performed by a computing system such as system 100, any components included therein, and/or any implementation thereof.

In operation 1102, a computing system obtains a visual image of an anatomical scene that includes an imaging probe. The visual image may be captured by a first imaging modality (e.g., an endoscope), and the computing system may obtain the visual image from the first imaging modality or any other suitable source. Operation 1102 may be performed in any of the ways described herein.

In operation 1104, the computing system augments the visual image with a preview placeholder indicating a display position for a probe image to be captured by the imaging probe. For example, the computing system may augment the visual image to form an augmented image such as any of the augmented images shown in FIGS. 6A-7B. Operation 1104 may be performed in any of the ways described herein.

In operation 1106, the computing system directs a display device to display the augmented image. To this end, the computing system may provide data representative of the augmented image to the display device for processing and display of the augmented image by the display device. Operation 1106 may be performed in any of the ways described herein.

In some examples, a non-transitory computer-readable medium storing computer-readable instructions may be provided in accordance with the principles described herein. The instructions, when executed by a processor of a computing device, may direct the processor and/or computing device to perform one or more operations, including one or more of the operations described herein. Such instructions may be stored and/or transmitted using any of a variety of known computer-readable media.

A non-transitory computer-readable medium as referred to herein may include any non-transitory storage medium that participates in providing data (e.g., instructions) that may be read and/or executed by a computing device (e.g., by a processor of a computing device). For example, a non-transitory computer-readable medium may include, but is not limited to, any combination of non-volatile storage media and/or volatile storage media. Illustrative non-volatile storage media include, but are not limited to, read-only memory, flash memory, a solid-state drive, a magnetic storage device (e.g. a hard disk, a floppy disk, magnetic tape, etc.), ferroelectric random-access memory ("RAM"), and an optical disc (e.g., a compact disc, a digital video disc, a Blu-ray disc, etc.). Illustrative volatile storage media include, but are not limited to, RAM (e.g., dynamic RAM).

Figure 12:
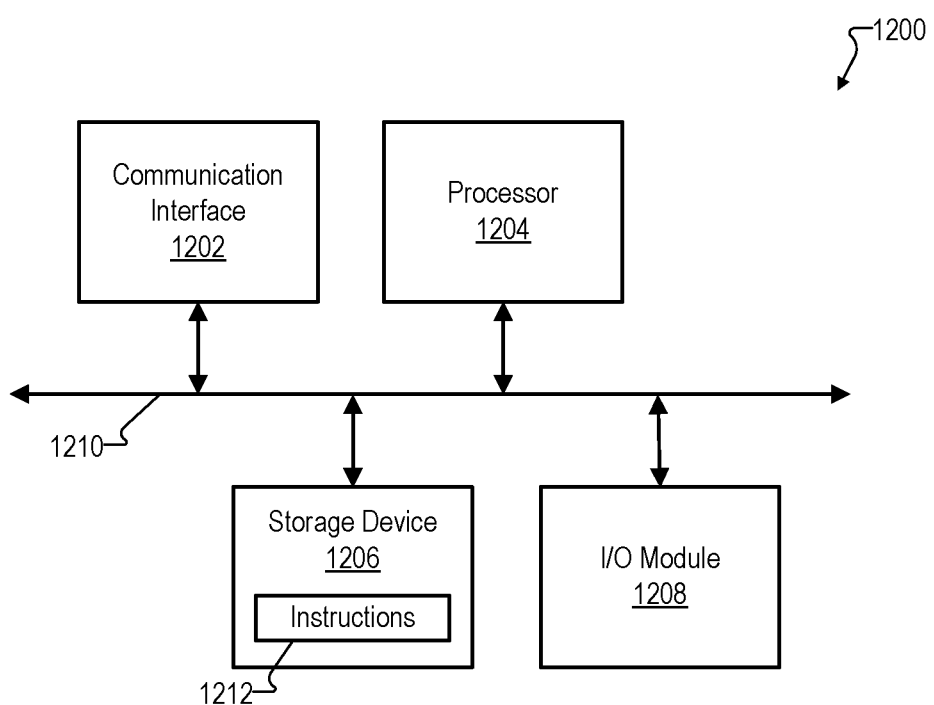
FIG. 12 depicts an illustrative computing device according to principles described herein.

FIG. 12 depicts an illustrative computing device 1200 that may be specifically configured to perform one or more of the processes described herein. Any of the systems, units, computing devices, and/or other components described herein may be implemented by computing device 1200.

As shown in FIG. 12, computing device 1200 may include a communication interface 1202, a processor 1204, a storage device 1206, and an input/output ("I/O") module 1208 communicatively connected one to another via a communication infrastructure 1210. While an illustrative computing device 1200 is shown in FIG. 12, the components illustrated in FIG. 12 are not intended to be limiting. Additional or alternative components may be used in other embodiments. Components of computing device 1200 shown in FIG. 12 will now be described in additional detail.

Communication interface 1202 may be configured to communicate with one or more computing devices. Examples of communication interface 1202 include, without limitation, a wired network interface (such as a network interface card), a wireless network interface (such as a wireless network interface card), a modem, an audio/video connection, and any other suitable interface.

Processor 1204 generally represents any type or form of processing unit capable of processing data and/or interpreting, executing, and/or directing execution of one or more of the instructions, processes, and/or operations described herein. Processor 1204 may perform operations by executing computer-executable instructions 1212 (e.g., an application, software, code, and/or other executable data instance) stored in storage device 1206.

Storage device 1206 may include one or more data storage media, devices, or configurations and may employ any type, form, and combination of data storage media and/or device. For example, storage device 1206 may include, but is not limited to, any combination of the non-volatile media and/or volatile media described herein. Electronic data, including data described herein, may be temporarily and/or permanently stored in storage device 1206. For example, data representative of computer-executable instructions 1212 configured to direct processor 1204 to perform any of the operations described herein may be stored within storage device 1206. In some examples, data may be arranged in one or more databases residing within storage device 1206.

I/O module 1208 may include one or more I/O modules configured to receive user input and provide user output. I/O module 1208 may include any hardware, firmware, software, or combination thereof supportive of input and output capabilities. For example, I/O module 1208 may include hardware and/or software for capturing user input, including, but not limited to, a keyboard or keypad, a touchscreen component (e.g., touchscreen display), a receiver (e.g., an RF or infrared receiver), motion sensors, and/or one or more input buttons.

I/O module 1208 may include one or more devices for presenting output to a user, including, but not limited to, a graphics engine, a display (e.g., a display screen), one or more output drivers (e.g., display drivers), one or more audio speakers, and one or more audio drivers. In certain embodiments, I/O module 1208 is configured to provide graphical data to a display for presentation to a user. The graphical data may be representative of one or more graphical user interfaces and/or any other graphical content as may serve a particular implementation.

In some examples, any of the systems and/or facilities described herein may be implemented by or within one or more components of computing device 1200. For example, one or more applications 1212 residing within storage device 1206 may be configured to direct an implementation of processor 1204 to perform one or more operations or functions associated with processing facility 104 of system 100.

One or more operations described herein may be performed or in real time. As used herein, operations that are described as occurring "in real time" will be understood to be performed immediately and without undue delay, even if it is not possible for there to be absolutely zero delay.

Any of the systems, devices, and/or components thereof may be implemented in any suitable combination or subcombination. For example, any of the systems, devices, and/or components thereof may be implemented as an apparatus configured to perform one or more of the operations described herein.

In the preceding description, various illustrative embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A system comprising:
a memory storing instructions; and
a processor communicatively coupled to the memory and configured to execute the instructions to:
obtain an endoscopic image of an anatomical scene within a body, the endoscopic image captured by an endoscope and depicting an imaging probe located at the anatomical scene, the imaging probe different from the endoscope;
augment the endoscopic image with a synthetic element that indicates, within the endoscopic image, an area of the anatomical scene being imaged by the imaging probe, the synthetic element including spatial markers within the area; and
direct a display device to display the augmented image.

2. The system of claim 1, wherein:
the synthetic element includes a border element outlining, within the endoscopic image, the area of the anatomical scene being imaged by the imaging probe; and
the spatial markers are positioned within the border element.

3. The system of claim 1, wherein the processor executes the instructions to:
obtain a probe image captured by the imaging probe; and
further augment the endoscopic image with a select portion of the probe image positioned within the area of the anatomical scene being imaged by the imaging probe.

4. The system of claim 1, wherein the processor executes the instructions to further augment the endoscopic image with a highlight element positioned to highlight a select portion of the area of the anatomical scene being imaged by the imaging probe.

5. The system of claim 1, wherein the processor executes the instructions to:
detect that the imaging probe is in a stationary state for a threshold amount of time; and
augment the endoscopic image with the synthetic element in response to detecting that the imaging probe is in the stationary state for the threshold amount of time.

6. The system of claim 1, wherein the processor executes the instructions to augment the endoscopic image with the synthetic element by performing operations comprising:
determining a pose of the imaging probe in the anatomical scene;
determining, based on the pose of the imaging probe, the area of the anatomical scene being imaged by the imaging probe; and
augmenting the endoscopic image with the synthetic element to visually indicate the area depicted in the endoscopic image.

7. The system of claim 1, wherein the processor executes the instructions to:
obtain a probe image captured by the imaging probe; and
direct the display device to display the probe image outside of the synthetic element.

8. The system of claim 7, wherein the processor executes the instructions to augment the probe image with an additional set of spatial markers that correspond to the spatial markers of the synthetic element.

9. The system of claim 7, wherein the processor executes the instructions to:
detect that the imaging probe is in a stationary state for a threshold amount of time; and
direct the display device to display the probe image in response to detecting that the imaging probe is in the stationary state for the threshold amount of time.

10. The system of claim 1, wherein the processor executes the instructions to further augment the endoscopic image with a preview placeholder indicating a display position for a probe image to be captured by the imaging probe.

11. A method comprising:
obtaining an endoscopic image of an anatomical scene within a body, the endoscopic image captured by an endoscope and depicting an imaging probe located at the anatomical scene, the imaging probe different from the endoscope;
obtaining a probe image captured by the imaging probe;
augmenting the endoscopic image with a synthetic element that indicates, within the endoscopic image, an area of the anatomical scene being imaged by the imaging probe; and
directing a display device to display the augmented image and the probe image, the probe image positioned outside of the synthetic element.

12. The method of claim 11, wherein the synthetic element includes:
a border element outlining, within the endoscopic image, the area of the anatomical scene being imaged by the imaging probe; and
spatial markers within the border element.

13. The method of claim 11, further comprising:
augmenting the endoscopic image with a select portion of the probe image positioned within the synthetic element.

14. The method of claim 11, further comprising:
augmenting the endoscopic image with a highlight element positioned within the synthetic element to highlight a select portion of the area of the anatomical scene.

15. The method of claim 11, further comprising:
detecting that the imaging probe is in a stationary state for a threshold amount of time; and
augmenting the endoscopic image with the synthetic element in response to detecting that the imaging probe is in the stationary state for the threshold amount of time.

16. The method of claim 11, wherein the augmenting of the endoscopic image with the synthetic element further comprises:
determining a pose of the imaging probe in the anatomical scene;
determining, based on the pose of the imaging probe, the area of the anatomical scene being imaged by the imaging probe; and
augmenting the endoscopic image with the synthetic element to visually indicate the area depicted in the endoscopic image.

17. The method of claim 11, wherein the probe image is positioned in a corner area of the endoscopic image.

18. The method of claim 11, wherein:
the synthetic element includes a first set of spatial markers; and
the probe image is augmented with a second set of spatial markers that correspond to the first set of spatial markers of the synthetic element.

19. A non-transitory computer-readable medium storing instructions that, when executed, direct a processor of a computing device to:
obtain an endoscopic image of an anatomical scene within a body, the endoscopic image captured by an endoscope and depicting an imaging probe located at the anatomical scene, the imaging probe different from the endoscope;

augment the endoscopic image with a synthetic element that indicates, within the endoscopic image, an area of the anatomical scene being imaged by the imaging probe, the synthetic element including spatial markers within the area; and direct a display device to display the augmented image;

wherein the synthetic element includes a border element outlining, within the endoscopic image, the area of the anatomical scene being imaged by the imaging probe; and the spatial markers are positioned within the border element.

20. The non-transitory computer-readable medium of claim 19, wherein the instructions, when executed, further operates to:

obtain a probe image captured by the imaging probe;

direct the display device to display the probe image outside of the synthetic element;

detect that the imaging probe is in a stationary state for a threshold amount of time; and direct the display device to display the probe image in response to detecting that the imaging probe is in the stationary state for the threshold amount of time.

* * * * *